US008653319B2

(12) United States Patent
Amery et al.

(10) Patent No.: US 8,653,319 B2
(45) Date of Patent: Feb. 18, 2014

(54) COLD IONIZING RADIATION STERILIZATION

(75) Inventors: Drew Powell Amery, Jacksonville, FL (US); Matthew F. Myntti, St. Augustine, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/989,150

(22) PCT Filed: Apr. 23, 2009

(86) PCT No.: PCT/US2009/041593
§ 371 (c)(1),
(2), (4) Date: Oct. 22, 2010

(87) PCT Pub. No.: WO2009/132229
PCT Pub. Date: Oct. 29, 2009

(65) Prior Publication Data
US 2011/0040226 A1 Feb. 17, 2011

Related U.S. Application Data

(60) Provisional application No. 61/047,580, filed on Apr. 24, 2008.

(51) Int. Cl.
A61F 13/00 (2006.01)
A61L 2/00 (2006.01)
A61K 9/00 (2006.01)

(52) U.S. Cl.
USPC .......... 602/42; 422/22; 424/400; 602/49

(58) Field of Classification Search
None
See application file for complete search history.

(56) References Cited

U.S. PATENT DOCUMENTS

| | | | |
|---|---|---|---|
| 4,137,200 A | 1/1979 | Wood et al. | |
| 5,012,503 A | 4/1991 | Nambu et al. | |
| 5,770,229 A | 6/1998 | Tanihara et al. | |
| 6,334,968 B1 | 1/2002 | Shapiro et al. | |
| 6,494,917 B1 | 12/2002 | McKellop et al. | |
| 7,259,192 B2 | 8/2007 | Liu et al. | |
| 2002/0064580 A1 | 5/2002 | Gord et al. | |
| 2002/0183855 A1* | 12/2002 | Yamamoto et al. | 623/23.51 |
| 2005/0003007 A1* | 1/2005 | Boix et al. | 424/486 |
| 2007/0031474 A1 | 2/2007 | Tayot | |
| 2007/0264296 A1 | 11/2007 | Myntti | |
| 2007/0264310 A1 | 11/2007 | Hissong et al. | |
| 2007/0267030 A1 | 11/2007 | Muratoglu et al. | |
| 2008/0008738 A1* | 1/2008 | Oliver et al. | 424/426 |
| 2008/0010947 A1 | 1/2008 | Huang et al. | |
| 2008/0098614 A1 | 5/2008 | Tchessalov et al. | |
| 2008/0215142 A1 | 9/2008 | Muratoglu et al. | |
| 2008/0299002 A1 | 12/2008 | Freeman et al. | |

FOREIGN PATENT DOCUMENTS

| | | |
|---|---|---|
| WO | WO 01/70279 A1 | 9/2001 |
| WO | WO 03/020771 A1 | 3/2003 |
| WO | WO 03/026704 A1 | 4/2003 |
| WO | WO 03/092745 A1 | 11/2003 |
| WO | WO 2004/009143 A1 | 1/2004 |
| WO | WO 2005/011752 A1 | 2/2005 |
| WO | WO 2008/008436 A1 | 1/2008 |
| WO | WO 2009/132225 A2 | 10/2009 |

OTHER PUBLICATIONS

Singh et al.; J. of Polymer Science: Part B: Polymer Physics, vol. 42, 1299-1311 (2004).*
Loo et al.; Biomaterials 26 (2005), pp. 1359-1367.*
Eastman Tritan™ copolyester, "*Redefining the balance between processability and chemical resistance*", Eastman Chemical Company, 12 pages, (Feb. 2009).
International Atomic Energy Agency, "*Trends in Radiation Sterilization of Health Care Products*", 278 pages, (Jul. 2008).
Haji-Saeid, M., et al., "*Radiation treatment for sterilization of packaging materials*", Radiation Physics and Chemistry 76 pp. 1535-1541 (2007).
Eastman Specialty Plastics, The Material Difference™ in Medical Applications, "*The Effect of Electron Beam Sterilization on Transparent Polymers Used in Medical Devices*", Eastman Chemical Company, 6 pages, (Jan. 2007).
Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004).
Krauland et al., *Viscoelastic Properties of a New in situ Gelling Thiolated Chitosan Conjugate*, Drug Development and Industrial Pharmacy, 31, 885-893 (2005).
Bernkop-Schnürch, *Thiomers: A new generation of mucoadhesive polymers*, Advanced Drug Delivery Reviews, 57, 1569-1582 (2005).
Bernkop-Schnürch et al., *Thiomers: Preparation and in vitro evaluation of a mucoadhesive nanoparticulate drug delivery system*, International journal of Pharmaceutics, 317, 76-81 (2006).

(Continued)

*Primary Examiner* — Robert A Wax
*Assistant Examiner* — Jeffrey T Palenik
(74) *Attorney, Agent, or Firm* — IPLM Group, P.A.

(57) ABSTRACT

A hydratable gel-forming polymer may be sterilized by chilling the polymer below ambient temperature and sterilizing the chilled polymer using ionizing radiation (e.g., E-Beam radiation). Doing so may reduce the degradation in physical properties caused by ionizing radiation sterilization of the polymer while at ambient temperature, and may preserve or retain desired hydration or gel-forming characteristics.

34 Claims, No Drawings

(56) References Cited

OTHER PUBLICATIONS

Dennis, Robert G., Sterilization, Disinfection, and Asepsis downloaded from the Internet Archive for Aug. 19, 2007 at http://liveweb.waybackmachine.org/http://www.bme.unc.edu/~bob/classes/senior-design/disinfection-sterilization-chapter.pdf.

Temperature-Controlled Sterilization Process (from E-BEAM Services, Inc.) downloaded from the Internet Archive for Oct. 8, 2007 at http://web.archive.org/web/20071008121952/www.ebeamservices.com/release0407b.htm.

Allen, Daphne, Sterilization: Conquering Sterilization Challenges, Pharmaceutical & Medical Packaging News, vol. 16, No. 5 (May 2008).

Choi, Jong-il, et al., Effect of electron beam irradiation on the viscosity of carboxymethylcellulose solution, Nuclear Instruments and Methods in Physics Research Section B: Beam Interactions with Materials and Atoms, vol. 266, Issue 23, pp. 5068-5071 (Dec. 2008).

Choi, Jong-il, et al., Controlling the radiation degradation of carboxymethylcellulose solution, Polymer Degradation and Stability vol. 93, pp. 310-315 (Jan. 2008).

Wach RA, et al., Hydrogel of biodegradable cellulose derivatives. II. Effect of some factors on radiation-induced crosslinking of CMC, Journal of Applied Polymer Science, vol. 81, Issue 12, pp. 3030-3037 (Sep. 19, 2001).

Gu et al., "The development of artificial articular cartilage-PVA-hydrogel", Bio-Medical Materials and Engineering 8, pp. 75-81 (1998).

* cited by examiner ated as WO 2009/132229 A2, which in turn claims priority from U.S. Provisional Application Ser. No. 61/047,580 filed Apr. 24, 2008 and entitled REHYDRATABLE POLYSACCHARIDE PARTICLES AND SPONGE.

COLD IONIZING RADIATION STERILIZATION

CROSS REFERENCE TO RELATED APPLICATIONS

This application is a U.S. national stage entry under 35 U.S.C. §371 of International Application No. PCT/US2009/041593 filed Apr. 23, 2009, entitled COLD IONIZING RADIATION STERILIZATION and published as WO 2009/132229 A2, which in turn claims priority from U.S. Provisional Application Ser. No. 61/047,580 filed Apr. 24, 2008 and entitled REHYDRATABLE POLYSACCHARIDE PARTICLES AND SPONGE.

FIELD OF THE INVENTION

This invention relates to polymer sterilization.

BACKGROUND

A variety of polymers have been employed to make surgical implants and tissue sealants, or to perform surgical repairs and drug delivery. In order to satisfy patient safety considerations and meet regulatory requirements, medical products containing such polymers normally are sterilized at the manufacturing site. A variety of sterilization techniques have been employed, including chemical treatments (e.g., ethylene oxide gas or hydrogen peroxide), heat (e.g., steam) and ionizing radiation (e.g., gamma radiation, ultraviolet light, X-ray or E-Beam processing).

Medical products containing polysaccharides or other polymers may be provided to a medical professional in dry hydratable form (e.g., as a powder or sponge), and hydrated (e.g., rehydrated) to form a moist shapeable product (e.g., a cohesive gel or compressible sponge) for subsequent placement in a patient.

SUMMARY OF THE INVENTION

In some cases a hydratable medical product is required to exhibit specific physical characteristics during or after hydration, or during or after patient placement. For example, a hydratable gel-forming polymer may require one or more properties such as rapid, clump-free hydration; thixotropic behavior when sprayed or injected; high viscosity and cohesive gel character once in place; controllable biodegradation; resistance to premature biodegradation; or an ability to break down or be dislocated without producing large solid chunks. A hydratable sponge may require one or more properties such as tensile strength; resiliency; slow or rapid shape recovery after being compressed; controllable biodegradation; resistance to premature biodegradation; or an ability to break down or be dislocated without producing large solid chunks. These properties may be strongly influenced by the polymer molecular weight. Sterilization using ionizing radiation may cause significant polymer chain scission and a substantial reduction in molecular weight, with a consequent substantial change in polymer properties. The degree of polymer degradation may be especially severe when using gamma radiation sterilization, but appreciable degradation may also be observed when using other ionizing radiation sterilization techniques. Sterilization using steam or ethylene oxide (which typically is performed in the presence of water vapor) may hydrate the polymer and prematurely convert it to a gel form, thereby limiting or preventing subsequent rehydration at an intended time for product placement.

The present invention provides, in one aspect, a method for polymer sterilization, which method comprises:
a) providing a hydratable gel-forming polymer chilled below ambient temperature (e.g., chilled to a temperature below about 15° C.); and
b) sterilizing the chilled polymer using ionizing radiation to provide a sterile polymer.

In a preferred embodiment the chilled polymer is sterilized using E-Beam radiation. The disclosed method can reduce polymer chain scission and physical property alteration compared to ionizing radiation sterilization of an ambient temperature polymer. The method is especially useful for maintaining acceptable physical properties for hydratable gel-forming polymers which will be sprayed onto a treatment site.

The invention provides in another aspect a medical device comprising a sterile hydratable gel-forming polymer whose polydispersity index is greater than that of the polymer if unsterilized (viz., that of the polymer before sterilization), or whose weight average or number average molecular weight is greater than the respective weight average or number average molecular weight of the polymer if sterilized using ionizing radiation (e.g., using E-Beam radiation) while at ambient temperature.

The invention provides in another aspect a treatment method, which method comprises hydrating the disclosed sterile hydratable gel-forming polymer to form a cohesive hydrogel, and injecting or spraying a layer of the cohesive hydrogel onto tissue (e.g., mucosal tissue) or other body structures.

DETAILED DESCRIPTION

The following detailed description describes certain embodiments and is not to be taken in a limiting sense. All weights, amounts and ratios herein are by weight, unless otherwise specifically noted. The terms shown below have the following meanings:

The term "ambient temperature" means normal room temperature, e.g., 20° C.

The term "antimicrobial" refers to an ability to cause greater than a 90% numeric reduction (viz., at least a 1-log order reduction) in a population of one or more of *Staphylococcus aureus, Pseudomonas aeruginosa, Streptococcus pneumonia, Haemophilus influenzae* or *Moraxella catarrhalis*.

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "bioresorbable" when used in reference to a substance means that the substance is capable of being absorbed by the body.

The term "cohesive" when used in reference to a liquid or gel means that the liquid or gel when placed on a level surface will tend to (but need not in all cases) stick to itself and form a unitary mass.

The term "comminuted" when used in reference to a particulate material means that the particles have been fractured and reduced in size by cutting, grinding, pulverizing, triturating or other particle fracturing process employing externally-applied force.

The term "fluid" when used in reference to a substance means that the substance is a liquid having a loss modulus (G") greater than its storage modulus (G') and a loss tangent (tan δ) greater than 1.

The term "gel" when used in reference to a substance means that the substance is deformable (viz., is not a solid), G" is less than G' and tan δ is less than 1.

The term "gelation" when used with respect to formation of a gel means the time at which G" equals G' and tan δ equals 1.

The term "hydratable gel-forming" when used in reference to a polymer means that the polymer when in dry form may be combined with water to form a cohesive hydrogel.

The term "hydrogel" when used in reference to a gel means that the gel is hydrophilic and contains water.

The term "hydrated" when used in reference to a device or substance means that the device or substance contains uniformly distributed chemically-bound water. A "fully hydrated" device or substance is incapable of taking up additional water of hydration. A "partially hydrated" device or substance is capable of taking up additional water of hydration.

The term "mucoadhesive" when used in reference to a device or substance means that the device or substance will adhere to the mucus covering epithelia.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx.

The terms "polydispersity" and "polydispersity index" mean the ratio Mw/Mn where Mw is the weight average molecular weight and Mn is the number average molecular weight, both measured using size exclusion chromatography with a multi-angle light scattering detector (SEC-MALS).

The term "polysaccharide" includes derivatives of polysaccharides and modified polysaccharides, as well as derivatives of individual polysaccharide species and modified individual polysaccharide species. For example, the term "carboxymethylcellulose" includes carboxymethylcellulose derivatives and modified carboxymethylcelluloses, the term "chitosan" includes chitosan derivatives and modified chitosans, and the term "starch" includes starch derivatives and modified starches.

The term "protective" when used in reference to a layer of a composition atop tissue or other body structure means that the layer may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a protective gel layer atop tissue or other body structure means the time period during which the gel layer or portion thereof remains in place in vivo under gross observation.

The term "solvating" means forming a solution or dispersion containing a solvent or other carrier within which a solute is dissolved or suspended.

The terms "sterile" and "sterilized" when used in reference to a device or substance mean that the device or substance is free from viable microorganisms when evaluated according to ISO standard 11135:1994(E), or that the device or method has a Sterility Assurance Level (SAL), determined based on the probability of a viable microorganism being present on a product unit after sterilization, less than $10 E^{-3}$. An "unsterile" device or substance is one which is not sterile, and an "unsterilized" device or substance is one which has not been subjected to a sterilization procedure.

The term "substantially collagen-free" means containing a sufficiently low amount of collagen so as not to pose a potential risk of transmission of or infection with bovine spongiform encephalopathy (BSE) or variant Creutzfeldt-Jakob disease (vCJD).

The term "thin" when used in reference to a protective layer atop tissue or other body structure means having an average thickness less than about two millimeters.

A wide variety of hydratable gel-forming polymers may be employed in the disclosed methods and medical devices. The polymer may be crosslinkable or uncrosslinkable, and one or all of the polymers in a mixture of polymers may be crosslinked. The polymer desirably is water soluble or may be rendered so, e.g., by suitable acidification. The polymer may be a liquid, gel or solid. If a liquid, the polymer desirably is crosslinkable and is combined with a suitable crosslinking agent to bring about gel formation. If a solid, the polymer desirably is in particulate form to facilitate more rapid hydration and gel formation, e.g., as free-flowing granules whose average particle diameter is less than about 1 mm, less than about 100 μm, about 1 to about 80 μm, or less than 1 μm. The polymer may have a variety of molecular weights, e.g., a weight average molecular weight before sterilization of about 7 to about 3000 kDa, about 15 to about 750 kDa, or about 15 to about 500 kDa and a number average molecular weight before sterilization of about 5 to about 2000 kDa, about 10 to about 500 kDa, or about 10 to about 300 kDa.

Compositions containing mixtures of polymers are especially desirable, as such compositions may enable formation of hydrogels and sponges whose properties could not be provided using a single polymer. For example, by altering the ratio of two polymers in a blend, the biodegradable or bioresorbable characteristics and residence time of the blend may be altered. A mixture of two polymers may for example contain about 99 to about 1% of a first polymer and about 1 to about 99% of a second polymer, or about 80 to about 20% of the first polymer and about 20 to about 80% of the second polymer, or about 60 to about 40% of the first polymer and about 40 to about 60% of the second polymer. Through appropriate selection of the types and amounts of polymers in a mixture, rehydratable gels and sponges with tunable properties may be obtained.

Exemplary polymers for use in the disclosed methods and medical devices include polyethylene glycols ("PEGs"), methoxypolyethylene glycols ("MPEGs") and other polyoxyethylenes; collagen and collagen derivatives including gelatin; polysaccharides and polysaccharide derivatives; hydratable polyurethanes and combinations thereof. Polyoxyethylenes and polysaccharides are especially desirable hydratable gel-forming polymers. Exemplary polyoxyethylenes include CARBOWAX™ polyethylene glycols from Dow Chemical Company, the corresponding CARBOWAX SENTRY™ food and drug compliant polyethylene glycols also from Dow Chemical Company and other biocompatible polyoxyethylenes capable of providing a hydratable gel-forming polymer.

Exemplary collagens and collagen derivatives are available from a variety of sources including processors of beef cattle and pigs. The disclosed medical device may be substantially collagen-free, and desirably is sufficiently free of collagen (e.g., containing no collagen at all) so as to be saleable worldwide for use without restriction in humans.

Exemplary polysaccharides include agars, alginates, carrageenans, celluloses, chitins, chitosans, chondroitin sulfates, dextrans, galactomannans, glycogens, hyaluronic acids, starches and other biocompatible polysaccharides capable of providing a hydratable gel-forming polymer. Compositions containing carboxymethyl cellulose (CMC) and chitosan may provide an especially desirable set of properties. Other desirable compositions include those containing chitosan together with an alginate, hyaluronic acid or chondroitin sulfate.

Exemplary celluloses include CMC, methylcellulose, ethylcellulose, hydroxypropyl cellulose, hydroxypropyl methyl cellulose and hemicellulose, as well as derivatives thereof including oxidized celluloses. Exemplary cellulosic materials may be obtained from a variety of commercial sources including Dow Wolff Cellulosics (e.g., the WALOCEL™ CRT line of sodium carboxymethylcellulose products), Hercules, Inc. (e.g., the AQUALON™ line of cellulose gum and carboxymethylcellulose products) and Sigma-Aldrich Co. (e.g., No. C4021 microgranular cellulose).

Exemplary unmodified chitosans and their salts (including citrate, nitrate, lactate, phosphate, chloride and glutamate salts) may be obtained from a variety of commercial sources including KitoZyme S.A., Fluka Chemie AG, the NovaMatrix unit of FMC BioPolymer AS and Sigma-Aldrich Co. Chitosan may also be synthesized by deacetylation of chitin (poly-N-acetyl-D-glucosamine) to eliminate acetyl groups on the nitrogen atom by hydrolysis. The resulting polymer has a plurality of repeating units (e.g., about 30 to about 3000 repeating units, about 60 to about 600 repeating units, or such other amount as may be desired for the chosen end use) some or all of which contain deacetylated amino groups (e.g., about 30 to about 100% or about 60 to about 95% of the total repeating units), with the remaining repeating units (if any) containing acetylated amino groups. The polymer is cationic and may be regarded as being composed from glucosamine monomers. The chitosan may for example be an ultralow molecular weight material having a number average molecular weight before sterilization less than about 50 kDa, a low molecular weight material having a number average molecular weight before sterilization of about 50 to about 200 kDa, a medium molecular weight material having a number average molecular weight before sterilization of about 200 to about 500 kDa or a high molecular weight material having a number average molecular weight before sterilization greater than about 500 kDa. Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolated reactant, e.g., as described in published PCT Application No. WO 03/020771 A1 and in Roldo et al., Mucoadhesive thiolated chitosans as platforms for oral controlled drug delivery: synthesis and in vitro evaluation, European Journal of Pharmaceutics and Biopharmaceutics, 57, 115-121 (2004), Krauland et al., Viscoelastic Properties of a New in situ Gelling Thiolated Chitosan Conjugate, Drug Development And Industrial Pharmacy, 31, 885-893 (2005), Bernkop-Schnürch, Thiomers: A new generation of mucoadhesive polymers, Advanced Drug Delivery Reviews, 57, 1569-1582 (2005) and Bernkop-Schnürch et al., Thiomers: Preparation and in vitro evaluation of a mucoadhesive nanoparticulate drug delivery system, International journal of Pharmaceutics, 317, 76-81 (2006).

Sources for and types of other polysaccharides (e.g., agars, alginates, carrageenans, chitins, chondroitin sulfates, dextrans, galactomannans, glycogens, hyaluronic acids, starches) may be chosen by persons skilled in the art based on selection characteristics similar to those given above for celluloses and chitosans. When combined in a polysaccharide mixture, the amounts of each polysaccharide may be varied widely to attain a desired combination of properties. For example, a blend of CMC and chitosan may have good bacteriostatic performance due to the chitosan and controlled, sustained and tunable degradation rates due to the CMC, whereas chitosan used alone may form a gel or sponge having inherently poor mechanical and resorbtive properties and CMC used alone may form a gel or sponge lacking bactericidal properties.

Exemplary hydratable polyurethanes include those described in U.S. Pat. No. 4,137,200, HYPOL™ hydrophilic polyurethane prepolymers (Dow Chemical Company, Midland Mich.) and NASOPORE™ nasal dressing from Polyganics BV, Rozenburglaan, The Netherlands).

The polymer(s) optionally are crosslinked before being packaged and sent to end users. Crosslinking may for example be carried out using a dehydrothermal crosslinking process as described in published PCT Application No. WO 2009/132225 A2, filed even date herewith. For the disclosed rehydratable gel this preferably is done by dehydrothermally crosslinking a mass of free-flowing rehydratable polymer particles to form free-flowing rehydratable crosslinked polymer particles. In other words, the particles preferably are themselves individually crosslinked while still remaining free-flowing and capable of later rapid dissolution and rehydration. For the disclosed sponge, crosslinking preferably is done by dehydrothermally crosslinking a shaped porous article which has been made by placing a solution of the desired polymer in a suitable mold and lyophilizing the solution to form a porous solid having a shape corresponding to the desired uncompressed sponge shape. In other words, the sponge preferably is shaped and made porous prior to crosslinking.

Crosslinking may also be performed using condensation reactions (e.g., a dehydration reaction leading to the loss of water, or a reaction leading to the loss of another small molecule such as hydrogen chloride, methanol or acetic acid), addition polymerization reactions (e.g. of vinyl groups), ionic reactions, or reactions involving sulfide or amine groups.

When combinations of two or more polymers are employed, crosslinking may be performed on one or on more than one of the polymers before the polymers are blended. This permits customization of properties such as gelation behavior, gelation time and degradation time following implantation. If desired, the resulting blend may be subjected to an additional crosslinking reaction, e.g., a dehydrothermal crosslinking reaction. The polymers may also be kept separate and later mixed by an end user, although this will normally be less convenient than forming the blend at a manufacturing site.

The disclosed hydratable gel-forming polymer is converted from an unsterile to a sterile form using cold ionizing radiation sterilization. The term "cold" refers in this context to the use of ionizing radiation to sterilize a polymer chilled below ambient temperature, and not to the use of ionizing radiation to sterilize a polymer at ambient temperature. It should be noted that E-Beam sterilization of polymers at ambient temperature is sometimes referred to in various publications as "cold" E-Beam sterilization to distinguish such sterilization from elevated temperature sterilization processes such as the use of steam or ethylene oxide. For the present application the term "cold E-Beam sterilization" will instead refer to the use of E-Beam radiation to sterilize a polymer chilled below ambient temperature.

The polymer may be chilled in a variety of ways, including storage in a freezer, contact with a cold plate, exposure to chilled dry air, exposure to dry ice or exposure to liquefied anhydrous gas (e.g., liquid carbon dioxide or liquid nitrogen). The polymer may for example be chilled to a temperature (as measured in the interior of the polymer sample prior to E-Beam exposure) at or below 15° C., 10° C., 5° C., 0° C., −5° C., −10° C., −15° C., −20° C., or even colder, e.g., as may be attained by chilling to temperatures approaching or at the dry ice atmospheric pressure sublimation point (−79° C.) or the liquid nitrogen atmospheric pressure boiling point (−196° C.). The sterile polymer may experience less polymer chain scission than an otherwise similar polymer sterilized using ionizing radiation while at ambient temperature. In general, as the chilled polymer temperature is reduced, the extent of polymer chain scission caused by ionizing radiation sterilization may likewise be reduced. Depending on the chosen sterilization technique, chilling may be carried out before and during sterilization or merely before sterilization. For a slower sterilization technique such as gamma radiation sterilization, chilling generally will be needed both before and during sterilization. For a faster sterilization technique such as E-Beam processing, chilling merely before sterilization may suffice.

A variety of ionizing radiation sterilization sources may be employed, including gamma radiation, ultraviolet light, X-rays and E-Beam radiation. E-Beam radiation is especially desirable due in part to the rapid rate at which it can be performed, with typical sterilization cycles usually being completed in a manner of minutes (e.g., two five minute cycles). X-rays may be preferred for applications where greater penetrating power than that provided by E-Beam radiation is required. Ultraviolet radiation and gamma radiation may also be employed, but may be contraindicated in some cases due in part to the higher degree of polymer degradation that ultraviolet or gamma radiation may cause and in the case of gamma radiation due to the much longer sterilization cycles (e.g., several hours or more) which may be required.

Cold E-Beam sterilization is as noted above especially desirable, and will be discussed below in greater detail. It should be understood that persons skilled in the sterilization art may substitute other cold ionizing radiation methods for cold E-Beam sterilization by suitable adaptation of the E-Beam discussion set out below.

The disclosed cold E-Beam sterilization method appears to reduce the polymer weight average and number average molecular weight values, but by less than may be observed if the polymer is sterilized using E-Beam radiation while the polymer is at ambient temperature. The disclosed method may provide reduced degradation or improved retention of polymer molecular weight and various other physical properties, e.g., shelf life, sprayability, cohesive strength, adhesive strength, or residence or retention time after placement at a treatment site. For example, a gel-forming polymer subjected to conventional (ambient temperature) E-Beam sterilization may no longer form a gel when sprayed, but the polymer gel-forming ability may be preserved when cold E-Beam sterilization is substituted for conventional E-Beam sterilization. The extent of observed change for any given physical property may depend on a variety of factors including the chosen polymer and its molecular weight and polydispersity index. The weight average or number average molecular weight following cold E-Beam sterilization may for example be at least 50%, at least 60%, at least 70% or at least 80% of the corresponding weight average or number average molecular weight for the unsterilized polymer. Cold E-Beam sterilization also may increase the polydispersity index over that of the unsterilized polymer, whereas conventional E-Beam sterilization may not alter or may reduce the polydispersity index compared to that of a polymer which has not been sterilized. For example, after cold E-Beam sterilization the sterilized polymer may have a polydispersity index at least 2%, at least 4% or at least 8% greater than that of the unsterilized polymer.

Suitable E-Beam sterilization devices or services are available from a variety of suppliers including BeamOne LLC (San Diego, Calif.), E-BEAM Services, Inc. (Cranbury, N.J.), Isotron (UK), L-3 Communication Pulse Sciences (San Leandro, Calif.), NUTEK Corporation (Hayward, Calif.) and Sterigenics International, Inc. (San Diego, Calif.). The desired E-Beam radiation dosage level may vary depending on the chosen polymer(s), the chosen product form (e.g., liquid, gel, particulate or sponge) and whether or not packaging is present, and generally will be determined empirically. Sufficient E-Beam radiation should be employed to ensure a sterile product, while avoiding levels that might cause excessive chain scission and polymer degradation. The chosen dosage may for example correspond to a deposited radiation energy of about 10 to about 100 kilogray (kGy), about 15 to about 50 kGy or about 20 to about 35 kGy.

For some polymers (e.g., those prone to oxidation), chain scission or degradation may be further reduced by carrying out sterilization under an inert atmosphere (e.g., under nitrogen or argon gas). Whether or not an inert atmosphere is employed, it is also desirable to carry out sterilization under dry conditions (e.g., under dry air, nitrogen or argon) as doing so helps discourage premature polymer hydration. Dry conditions may also be facilitated by carrying out sterilization at or below 0° C., so that stray water vapor or moisture will tend to condense and freeze on nearby cold surfaces rather than causing premature polymer hydration.

Before or following sterilization the disclosed medical device may be placed in suitable sealed packaging (e.g., a syringe, vial or bag made of a suitable material) and stored as need be or shipped to a distributor or to an end user (e.g., a surgeon, physician, dentist or other medical professional). In a preferred embodiment the medical device is sealed in suitable packaging prior to chilling or prior to sterilization so that both the device and its packaging will be in sterile form when shipped to a distributor or end user. Depending on the desired end use, the chosen packaging may include a variety of features, e.g., sterilization maintenance, shelf life indication, shelf life preservation, tamper prevention, space for labels or warnings, sufficient clarity so that the contents may be viewed or inspected, indication of tampering, indication of sterility loss, and the like.

The disclosed medical device may be rehydrated prior to placement or insertion in a treatment site, or may be placed while in a dry state and then rehydrated in situ (e.g., via the addition of an externally-supplied rehydrating fluid, by the uptake of endogenous fluids, or both). Rehydrating a sponge normally is relatively straightforward, and may be carried out by immersing or saturating the sponge with water or an aqueous solution containing any other desired ingredients. For example, normal saline solution may be a preferred and readily available rehydration solution, and other materials such as phosphate buffered saline (PBS) may be used if desired. Rehydrating rehydratable gel particles may be somewhat more difficult due to the tendency of some dry powdered materials to form clumps when combined with water. Clumping may however be avoided using a rehydration procedure described in the above-mentioned published PCT Application No. WO 2009/132225 A2, in which rehydratable gel particles are dispersed in a biocompatible water-miscible polar dispersant (e.g., ethanol, isopropanol or acetone), followed by mixing the dispersion with sufficient aqueous particle solvent (viz., a water-based solvent for the particles) to convert the particles to a cohesive hydrogel. The polar dispersant is a sufficiently poor solvent for the particles so that the mixture of particles and dispersant will not form a true solution. The particles in such a dispersion desirably are sufficiently small so that the dispersion is stable or quasi-stable (e.g., a colloidal dispersion or a reasonably persistent suspension) after the particles and dispersant have been agitated, e.g., by swirling them together. Without being bound by theory, the addition of the aqueous particle solvent is believed to permit rehydration to occur approximately simultaneously at the surface of each suspended particle via dissolution of the surrounding dispersant into the aqueous particle solvent phase, thereby permitting formation of a cohesive hydrogel without forming visible clumps of unhydrated polymer. In this fashion a dispersed hydratable polymer (e.g., a dispersed polysaccharide) may be combined with water or an aqueous solution to form a clump-free hydrogel even though the dry powdered polymer would not ordinarily do so. In many instances the disclosed method may be used to prepare a satisfactory clump-free gel using passage between two syringes, mild agitation or other simple mixing techniques without requiring the use of a mechanical stirrer. The disclosed mixing method may also permit formation of very concentrated hydrogels which could not be obtained by merely mixing a powdered hydratable polymer with water, or with water to which an acid or base has been added.

When a cohesive hydrogel is prepared from a powdered hydratable polymer, the polymer concentration typically will depend on the chosen polymer molecular weight, and may for example be about 1 to about 20%, about 1 to about 10% or about 1 to about 5% of the rehydrated gel. The gel may desirably form in less than 30 minutes, less than 20 minutes, less than 10 minutes, less than 5 minutes, less than 1 minute or even essentially immediately after rehydration. For polymers which do not immediately rehydrate, it may be desirable to saturate the powder and inject it before the polymer has become too viscous to spray or otherwise dispense through a small orifice, e.g., through the spray tip employed in a No. SA-3668 FIBRIJET™ 360° Gas Assisted Endoscopic Applicator (Micromedics, Inc., St. Paul, Minn.).

The disclosed medical device may optionally include a variety of other ingredients before or after rehydration. Exemplary other ingredients include solvents, acids, bases, buffering agents, antimicrobial agents, therapeutic agents and other adjuvants. An acid, base or buffering agent may for example maintain a gel at an appropriate pH for contacting human tissue, e.g., a pH greater than 5, a near-neutral pH, or a pH less than 8.5. Exemplary buffering agents include barbitone sodium, glycinamide, glycine, potassium chloride, potassium phosphate, potassium hydrogen phthalate, sodium acetate, sodium citrate, sodium phosphate and their conjugate acids.

The disclosed medical device desirably is inherently antimicrobial without requiring addition of a separate antimicrobial agent. A separate antimicrobial agent may be employed if desired. A useful list of such antimicrobial agents may be found, for example, in U.S. Patent Application Publication No. US 2007/0264296 A1.

Exemplary therapeutic agents which may be employed in the disclosed medical device include any material suitable for use at the intended treatment site including analgesics, anticholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may be found, for example, in the above-mentioned U.S. Patent Application Publication No. US 2007/0264296 A1.

Other adjuvants that may be included in the disclosed medical device include dyes, pigments or other colorants (e.g., FD & C Red No. 3, FD & C Red No. 20, FD & C Yellow No. 6, FD & C Blue No.2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and rheology modifiers including thickeners and thixotropes. The disclosed medical device desirably does not contain ingredients which might potentially harm patient tissues or structures, e.g., mucosal tissues in the nasal or sinus cavities.

In those instances where it is desirable to remove water from tissue, e.g., to remove fluid from polyps or edematous tissue, a hyperosmolar agent may be employed in the disclosed medical device. Exemplary hyperosmolar agents include furosemide, sodium chloride gel and other salt preparations which draw water from tissue, and other substances which directly or indirectly change the osmolar content of the mucous layer. Where sustained release or delayed release of a therapeutic agent is desirable, a release agent modifier may also be included.

An applied rehydrated gel may fill the treatment site (e.g., a nasal or sinus cavity, or an opening, recess, passageway or joint in a portion of the limbs or spinal column), in which case the disclosed gel may form a layer which is very thick and not exposed to air or other nearby gases, and with differing thicknesses throughout the layer. The disclosed rehydrated gel may also be applied as a thin film or other conformal coating in which case the gel layer may form a layer which is relatively thin and exposed to air or other nearby gases, and with a substantially uniform thickness throughout the layer. The rehydrated gel may provide a protective layer which may be viscous, elastic or viscoelastic. The protective layer desirably adheres to mucosal or other natural tissues (e.g., cartilage or bone) at the treatment site and resists detachment or other disruption until natural degradation or resorption of the gel layer takes place, e.g., after a residence time in vivo of from one day to a few (e.g., 2, 3 or 4) days, weeks or months. Meanwhile bacterial recolonization or reinfection may be significantly reduced or prevented, and improved healing and reciliation may take place. The protective gel layer may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (e.g., specifically reducing the chronic inflammation related to bacterial toxin and the encapsulated polysaccharide in a bacterial biofilm), f) coating and protecting tissue during healing, such as by maintenance of a moist wound which promotes platelet aggregation, or by closure of a dry wound without excessive scabrous formation, g) hemostasis, h) optimizing the environment for reciliation of the mucosa, i) speeding the growth or regrowth of cilia and j) delivering therapeutic agent(s) to the treatment site. Desirably the protective gel layer will adhere to a portion of the mucosa while leaving the cilia in unadhered portions free to undergo natural rhythmic cilia motion (viz., cilia beating), will if desired also deliver antimicrobial agents or additional therapeutic agents, and desirably will discourage or prevent bacteria from adhering to the treatment site.

The disclosed medical device may desirably be used as a part of a multi-step treatment regimen which disrupts a bacterial biofilm and discourages its return. For example, a series of steps that may be broadly classified as Cleansing/Disrupting, Killing, Aerating, Protecting/Coating, and Healing may be carried out. The Cleansing/Disrupting step may be carried out by administering a solvating system as discussed in the above-mentioned U.S. Patent Application Publication No. US 2007/0264296 A1. The Killing step may be carried out by applying a suitable antimicrobial agent to the treatment site. This may for example be accomplished by including an antimicrobial agent in the solvating system, as a separately-applied composition, or in both the solvating system and in a separately-applied composition. An antimicrobial agent may also be applied or administered post operatively. The Aerating step may be carried out by providing air passageways or improving air passageways to the treated tissues by opening occluded or partially occluded passages, e.g., the sinuses or sinus ostia for nasal applications. This may for example be accomplished by surgically removing obstructive tissue structures or by manually displacing such structures. The Protecting/Coating step may be carried out by coating at least part of the thus-treated tissue with the disclosed gel composition or by covering at least part of the thus-treated tissue with the disclosed sponge. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal function. The multi-step treatment regimen may include or be followed by a Clearing step in which the gel composition or sponge is sufficiently biodegradable or bioresorbable to disappear from the treatment site in a desired time period, e.g., more than 1 day, more than 3 days, or about 4 to 7 days, and desirably without shedding large solid chunks. The disclosed method may advantageously be accomplished without requiring surgery, for example by applying and removing the optional solvating system through normal aspiration/suction techniques or by simple flushing of affected tissue followed by application of the disclosed gel composition or sponge. A comparable series of steps may be performed in a multi-step treatment regimen in a portion of the middle or inner ear. Further details regarding such a regimen may be found in U.S. Patent Application Publication No. US 2007/0264310 A1.

The invention is further illustrated in the following non-limiting examples.

EXAMPLE 1

Samples of a low molecular weight hydratable gel-forming polysaccharide polymer (PROTASAN™ G113 170,000 kDa chitosan glutamate from the NovaMatrix unit of FMC BioPolymer AS) and a medium molecular weight hydratable gel-forming polysaccharide polymer (PROTASAN G213 350,000 kDa chitosan glutamate from the NovaMatrix unit of FMC BioPolymer AS) were solubilized in PBS at a 5 wt. % polymer concentration and then lyophilized to form dry powders. An unsterilized portion of each sample was evaluated to determine Mw, Mn and the polydispersity index via SEC-MALS using TSK-GEL™ G6000PWx$_{XL}$, G5000PW$_{XL}$ and G3000PW$_{XL}$ size exclusion chromatography columns from Tosoh corporation (Japan), a WATERS™ 2695 Separation Module from Waters Corp. (Milford, MA), a WATERS 2414 DRI Detector from Waters Corp., a DAWN HELEOS™ multi-angle light scattering detector from Wyatt Technology Corp. (Santa Barbara, CA) and ASTRA™ V SP macromolecular characterization software from Wyatt Technology Corp. Portions of each sample stored at about 24° C. and portions chilled using a freezer to −20 to −25° C. were sterilized using E-Beam radiation at a dose of 25 kGy and evaluated to determine Mw, Mn and the polydispersity index. The results are shown below in Table 1:

TABLE 1

| Run No. | Sample | Mw, kDa | Mw, sterilized as a percent of unsterilized | Mn, kDa | Mn, sterilized as a percent of unsterilized | Poly-dispersity Index |
|---|---|---|---|---|---|---|
| 1 | G113, Unsterilized | 170 | — | 99 | — | 1.71 |
| 2 | G113, Sterilized Ambient | 100 | 59% | 59 | 59% | 1.70 |
| 3 | G113, Sterilized Frozen | 120 | 71% | 65 | 66% | 1.84 |
| 4 | G213, Unsterilized | 350 | — | 212 | — | 1.65 |
| 5 | G213, Sterilized Ambient | 140 | 40% | 88 | 41% | 1.60 |
| 6 | G213, Sterilized Frozen | 180 | 51% | 103 | 49% | 1.74 |

The results in Table 1 show that freezing the polymer before E-Beam sterilization resulted in considerably better molecular weight retention than was observed if the polymer was E-Beam sterilized while at ambient temperature.

The Table 1 samples were also evaluated to determine their spray characteristics. Each sample was dissolved in water at a 5% concentration. Using the above-mentioned No. SA-3668 FIBRIJET™ 360° Gas Assisted Endoscopic Applicator, the resulting solutions were sprayed onto a horizontal surface together with a 5 wt. % solution of oxidized starch. The unsterilized materials (viz., Run No. 1 and Run No. 4) formed non-dripping gels, with the unsterilized G113 sample of Run No. 1 providing better gelation and spray properties than the G213 sample of Run No. 4. After ambient or cold E-Beam sterilization, the G113 samples (viz., Run No. 2 and Run No. 3) formed gels which were less viscous than those obtained using the unsterilized G113 sample of Run No. 1, and exhibited longer gelation times. The Run No. 2 and Run No. 3 samples also exhibited a tendency to drip. The gel made using the cold E-Beam sterilized sample of Run No. 3 exhibited greater viscosity and less tendency to drip than a gel made using the ambient E-Beam sterilized sample of Run No. 2.

The ambient or cold E-Beam sterilized G213 samples (viz., Run No. 5 and Run No. 6) formed gels which were less viscous than those obtained using the unsterilized G213 sample of Run No. 4. The Run No. 4 and Run No. 5 samples did not drip, but the Run No. 5 sample had a slow gelation time. The gel made using the cold E-Beam sterilized sample of Run No. 6 exhibited the best balance of spray properties, gel formation, absence of dripping and gelation time among the sterilized product samples evaluated.

EXAMPLE 2

Using the method of Example 1, gels made from lyophilized carboxy methyl-chitosan were evaluated to determine their spray, drip and gelation characteristics following ambient or cold E-Beam sterilization. After ambient temperature E-Beam sterilization, the gel thickened noticeably and behaved poorly when sprayed. After cold E-Beam sterilization, the gel had slightly lower viscosity and performed acceptably when sprayed.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. A method for polymer sterilization, which method comprises:

a) providing a dry hydratable gel-forming polymer chilled below ambient temperature, the polymer having a weight average molecular weight before sterilization of at least about 7 kDa; and b) sterilizing the chilled polymer using ionizing radiation while the polymer is chilled below ambient temperature, to provide a sterile hydratable gel-forming polymer whose polydispersity index is greater than that of the polymer if it has not been sterilized, or whose weight average or number average molecular weight is greater than the respective weight average or number average molecular weight of the polymer if sterilized using ionizing radiation while at ambient temperature.

2. A method according to claim 1 wherein the sterile polymer has less polymer chain scission than the polymer if sterilized at ambient temperature using ionizing radiation.

3. A method according to claim 1 wherein the sterile polymer has higher polydispersity than the polymer if it has not been sterilized.

4. A method according to claim 1 wherein the sterile polymer is sterilized using E-Beam radiation and has higher polydispersity than the polymer if sterilized using E-Beam radiation while at ambient temperature.

5. A method according to claim 1 wherein the sterile polymer is sterilized using E-Beam radiation and has a higher weight average molecular weight than the polymer if sterilized using E-Beam radiation while at ambient temperature.

6. A method according to claim 1 wherein the sterile polymer has a weight average or number average molecular weight at least 60% of the corresponding weight average or number average molecular weight before sterilization.

7. A method according to claim 1 wherein the sterile polymer has a weight average or number average molecular weight at least 70% of the corresponding weight average or number average molecular weight before sterilization.

8. A method according to claim 1 wherein the sterile polymer has a weight average or number average molecular weight at least 80% of the corresponding weight average or number average molecular weight before sterilization.

9. A method according to claim 1 wherein the sterile polymer has a polydispersity index at least 2% greater than that of the polymer before sterilization.

10. A method according to claim 1 wherein the sterile polymer has a polydispersity index at least 4% greater than that of the polymer before sterilization.

11. A method according to claim 1 wherein the sterile polymer has a polydispersity index at least 8% greater than that of the polymer before sterilization.

12. A method according to claim 1 wherein the sterile polymer is a particulate.

13. A method according to claim 1 wherein the sterile polymer is non-comminuted.

14. A method according to claim 1 wherein a hydrogel prepared using the sterile polymer is sprayable and when so sprayed will form a gel.

15. A method according to claim 1 wherein the sterile polymer is a sponge.

16. A method according to claim 1 wherein the polymer comprises a polysaccharide.

17. A method according to claim 1 wherein the polymer comprises chitosan.

18. A method according to claim 1 wherein the polymer comprises a mixture of chitosan and another polysaccharide.

19. A method according to claim 1 wherein the polymer comprises a mixture of chitosan and carboxymethylcellulose.

20. A method according to claim 1 wherein the polymer comprises a polyethylene glycol.

21. A medical device comprising a sterile dry hydratable gel-forming polymer, which sterile polymer is prepared by a method comprising:

a) providing a dry hydratable gel-forming polymer chilled below ambient temperature, the polymer having a weight average molecular weight before sterilization of at least about 7 kDa; and b) sterilizing the chilled polymer using ionizing radiation while the polymer is chilled below ambient temperature, to provide a sterile hydratable gel-forming polymer whose polydispersity index is greater than that of the polymer if it has not been sterilized, or whose weight average or number average molecular weight is greater than the respective weight average or number average molecular weight of the polymer if sterilized using ionizing radiation while at ambient temperature.

22. A treatment method, which method comprises:

a) hydrating a gel-forming polymer to form a cohesive hydrogel, and b) injecting or spraying a layer of the cohesive hydrogel onto tissue or other body structure wherein said polymer is prepared by:

i) providing a dry hydratable gel-forming polymer chilled below ambient temperature, the polymer having a weight average molecular weight before sterilization of at least about 7 kDa; and ii) sterilizing the chilled polymer using ionizing radiation while the polymer is chilled below ambient temperature, to provide a sterile hydratable gel-forming polymer whose polydispersity index is greater than that of the polymer if it has not been sterilized, or whose weight average or number average molecular weight is greater than the respective weight average or number average molecular weight of the polymer if sterilized using ionizing radiation while at ambient temperature.

23. A method according to claim 1 wherein the dry hydratable gel-forming polymer is chilled below about 15° C.

24. A method according to claim 1 wherein the dry hydratable gel-forming polymer is chilled below about 0° C.

25. A method according to claim 1 wherein the dry hydratable gel-forming polymer is chilled below about −20° C.

26. A method according to claim 1 wherein the ionizing radiation is E-Beam radiation.

27. A method according to claim 1 further comprising sterilizing the chilled polymer under an inert atmosphere.

28. A method according to claim 1 wherein the dry hydratable gel-forming polymer has a weight average molecular weight before sterilization of about 7 to about 3000 kDa.

29. A method according to claim 1 wherein the dry hydratable gel-forming polymer has a weight average molecular weight before sterilization of about 15 to about 750 kDa.

30. A device according to claim 21 wherein the polymer comprises a polysaccharide.

31. A device according to claim 21 wherein the polymer comprises chitosan.

32. A device according to claim 21 wherein the polymer comprises a mixture of chitosan and another polysaccharide.

33. A device according to claim 21 wherein the polymer comprises a mixture of chitosan and carboxymethylcellulose.

34. A device according to claim 21 wherein the polymer comprises a polyethylene glycol.

* * * * *